United States Patent [19]
Habib et al.

[11] 4,361,707
[45] Nov. 30, 1982

[54] PROCESS FOR PRODUCING ALDEHYDES
[75] Inventors: Mohammad M. Habib, Allison Park; Wayne R. Pretzer, Gibsonia, both of Pa.
[73] Assignee: Gulf Research & Development Company, Pittsburgh, Pa.
[21] Appl. No.: 289,418
[22] Filed: Aug. 3, 1981
[51] Int. Cl.³ .............................................. C07C 45/49
[52] U.S. Cl. .................................. 568/487; 568/454; 568/882; 568/909
[58] Field of Search ............... 568/487, 454, 496, 882
[56] References Cited
U.S. PATENT DOCUMENTS 4,152,208  4/1979   Pretzer et al. ...................... 568/487
4,190,729  2/1980   Forster ................................ 568/487
4,239,704  12/1980  Pretzer et al. ...................... 568/487
4,239,705  12/1980  Pretzer et al. ...................... 568/487
4,262,154  4/1981   Gane et al. .......................... 568/487
4,293,718  10/1981  Gauthier-Lafaye et al. ....... 568/487

Primary Examiner—Werren B. Lone
Attorney, Agent, or Firm—Deane E. Keith; Forrest D. Stine; Joseph J. Carducci

[57] ABSTRACT

A process for selectively producing aldehydes, particularly acetaldehyde, which comprises introducing into a reaction zone (1) methanol, (2) carbon monoxide, (3) hydrogen, (4) cobalt, (5) iodine and (6) a specific phosphorus-containing ligand and then subjecting the contents of said reaction zone to an elevated temperature and an elevated pressure for a time sufficient to convert methanol to said aldehydes.

24 Claims, No Drawings

PROCESS FOR PRODUCING ALDEHYDES

BACKGROUND OF THE INVENTION

1. Field of the Invention

This invention is directed to a process for selectively producing aldehydes, particularly acetaldehyde, which comprises introducing into a reaction zone (1) methanol, (2) carbon monoxide, (3) hydrogen, (4) cobalt, (5) iodine, and (6) a specific phosphorus-containing ligand and then subjecting the contents of said reaction zone to an elevated temperature and an elevated pressure for a time sufficient to convert methanol to said aldehydes.

2. Description of the Invention

In European Patent Application No. 79302053.8, filed in the names of B. R. Gane and D. G. Stewart and published on April 30, 1980, it is disclosed that when methanol is reacted with synthesis gas in the presence of a catalyst comprising (a) cobalt, (b) an iodide or a bromide and (c) a polydentate ligand, wherein the donor atoms are exclusively phosphorus, the product obtained will contain a substantial proportion of ethanol. When the polydentate ligand used is one wherein at least one of the donor atoms is phosphorus and another is arsenic, it is alleged by Gane et al that the product will contain a mixture of ethanol and acetaldehyde.

SUMMARY OF THE INVENTION

We have found that if we introduce into a reaction zone (1) methanol, (2) carbon monoxide, (3) hydrogen, (4) cobalt, (5) iodine, and (6) a specific phosphorus-containing ligand, while controlling the proportion of the reaction components and the reaction parameters, we can obtain a reaction product predominating in aldehydes, including compounds convertible thereto, particularly acetaldehyde. By "compounds convertible thereto" we mean to include acetals, such as dimethyl acetal. In general the reaction product will contain at least about 30 weight percent, especially from about 35 to about 85 weight percent, of aldehydes and compounds convertible thereto. The acetaldehyde content of the reaction product will be at least about 25 weight percent, especially about 27 to about 75 weight percent. At the same time, the alcohol content of the reaction product, including compounds convertible thereto, will be very small. By "compounds convertible thereto", in the latter instance, we mean to include acetates, such as ethyl acetate. In general the reaction product will contain less than about 22 weight percent of alcohols and compounds convertible thereto, but more often from about two to about ten weight percent of alcohols and compounds convertible thereto. As to the ethanol content of the reaction product it will be less than about 18 weight percent, but more often in the range of about 0 to about seven weight percent. The compounds referred to above that can be converted to aldehydes or alcohols can be converted thereto by any known or suitable process, for example, by hydrolysis, that is, contacting a precursor thereof with water, with or without an acid (sulfuric) or a basic (sodium hydroxide) catalyst.

The phosphorus-containing ligand used herein can be defined by the following formula:

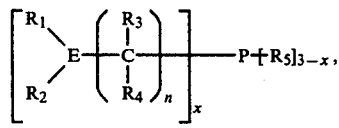

wherein $R_1$, $R_2$ and $R_5$ are either alike or different members selected from the group consisting of alkyl radicals having from one to 24 carbon atoms, preferably from two to 10 carbon atoms; aryl radicals having from six to 20 carbon atoms, preferably from six to 10 carbon atoms; alkenyl radicals having from two to 30 carbon atoms, preferably from two to 20 carbon atoms; cycloalkyl radicals having from three to 40 carbon atoms, preferably from three to 30 carbon atoms; aralkyl and alkaryl radicals having from six to 40 carbon atoms, preferably from six to 30 carbon atoms, and dihydrocarbyl phosphino alkyl radicals, such as

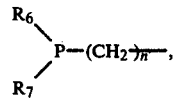

wherein n' is 1, 2 or 3, preferably 1 or 2, and $R_6$ and $R_7$ are alkyl or aryl, as defined above, preferably aryl or alkyl; $R_3$ and $R_4$ are either alike or different members selected from the group consisting of $R_1$, $R_2$ and $R_5$, defined above, and hydrogen, preferably hydrogen or alkyl; E can be phosphorus or arsenic, preferably phosphorus; n is an integer ranging from 1 to 3, preferably 2 to 3, but most preferably 2; and x can be 1, 2 or 3. Included among the phosphorus-containing ligands that can be employed herein, some of which are believed to be novel, are those defined below in Table I, referring to the structural formula hereinabove defined:

TABLE I

| | $R_1$ | $R_2$ | $R_3$ | $R_4$ | $R_5$ | E | n | x |
|---|---|---|---|---|---|---|---|---|
| 1. | Phenyl | Phenyl | Hydrogen | Hydrogen | Phenyl | P | 1 | 1 |
| 2. | Ethyl | Ethyl | Hydrogen | Hydrogen | Phenyl | P | 1 | 1 |
| 3. | Phenyl | Phenyl | Hydrogen | Hydrogen | Phenyl | P | 2 | 1 |
| 4. | Ethyl | Ethyl | Hydrogen | Hydrogen | Phenyl | P | 2 | 1 |
| 5. | Ethyl | Ethyl | Hydrogen | Hydrogen | Ethyl | P | 2 | 1 |
| 6. | Phenyl | Phenyl | Hydrogen | Hydrogen | Phenyl | As | 1 | 1 |
| 7. | Phenyl | Phenyl | Hydrogen | Hydrogen | Ethyl | As | 1 | 1 |
| 8. | Phenyl | Phenyl | Hydrogen | Hydrogen | Phenyl | As | 2 | 1 |
| 9. | Ethyl | Ethyl | Hydrogen | Hydrogen | Ethyl | As | 2 | 1 |
| 10. | Phenyl | Phenyl | Hydrogen | Hydrogen | Phenyl | P | 3 | 1 |
| 11. | Ethyl | Ethyl | Hydrogen | Hydrogen | Ethyl | P | 3 | 1 |
| 12. | Phenyl | Phenyl | Hydrogen | Hydrogen | Phenyl | As | 3 | 1 |
| 13. | Ethyl | Ethyl | Hydrogen | Hydrogen | Phenyl | As | 3 | 1 |
| 14. | Cyclohexane | Cyclohexane | Hydrogen | Hydrogen | Cyclohexane | P | 1 | 1 |
| 15. | Cyclohexane | Cyclohexane | Hydrogen | Hydrogen | Cyclohexane | P | 2 | 1 |
| 16. | Cyclohexane | Cyclohexane | Hydrogen | Hydrogen | Cyclohexane | P | 3 | 1 |
| 17. | P—tolyl | P—tolyl | Hydrogen | Hydrogen | P—tolyl | P | 2 | 1 |
| 18. | P—tolyl | P—tolyl | Hydrogen | Hydrogen | P—tolyl | As | 3 | 1 |

TABLE I-continued

| | R₁ | R₂ | R₃ | R₄ | R₅ | E | n | x |
|---|---|---|---|---|---|---|---|---|
| 19. | Phenyl | Phenyl | Methyl | Hydrogen | Phenyl | P | 2 | 1 |
| 20. | Phenyl | Phenyl | Methyl | Methyl | Phenyl | P | 2 | 1 |
| 21. | Ethyl | Ethyl | Methyl | Methyl | Ethyl | P | 2 | 1 |
| 22. | Phenyl | Phenyl | Hydrogen | Hydrogen | Phenyl | P | 2 | 2 |
| 23. | Ethyl | Ethyl | Hydrogen | Hydrogen | Ethyl | P | 2 | 2 |
| 24. | Ethyl | Ethyl | Methyl | Hydrogen | Ethyl | P | 2 | 2 |
| 25. | Phenyl | Phenyl | Hydrogen | Hydrogen | — | P | 2 | 3 |
| 26. | Ethyl | Ethyl | Hydrogen | Hydrogen | — | P | 2 | 3 |
| 27. | Phenyl | Phenyl | Methyl | Hydrogen | — | P | 2 | 3 |
| 28. | Phenyl | Phenyl | Hydrogen | Hydrogen | Phenyl | As | 2 | 2 |
| 29. | Phenyl | Phenyl | Hydrogen | Hydrogen | — | As | 2 | 3 |
| 30. | Phenyl | Phenyl | $(CH_3)_2PCH_2-$ | Methyl | Phenyl | P | 2 | 1 |
| 31. | Ethyl | Ethyl | $(CH_3)_2PCH_2-$ | Methyl | Ethyl | P | 2 | 1 |
| 32. | Phenyl | Phenyl | Methyl | $(C_6H_5)_2PCH_2-$ | Phenyl | P | 3 | 1 |
| 33. | $R_1 = R'_1 =$ Phenyl | Phenyl $R'_2 =$ $(C_6H_5)_2PCH_2CH_2-$ | Hydrogen | Hydrogen | Phenyl | P | 2 | 2 |

Any source of iodine which is capable of dissociating, that is, ionizing to form free iodide ions in the reaction medium can be used in the present invention. Illustrative examples of iodine compounds especially suitable for use herein include iodine, potassium iodide, calcium iodide, sodium iodide, lithium iodide, aluminum iodide, bismuth iodide, hydrogen iodide, methyl iodide, ethyl iodide, etc., and mixtures thereof.

The cobalt entity suitable for use herein can be defined as being a cobalt carbonyl, a hydrido cobalt carbonyl or a cobalt-containing compound convertible to a cobalt carbonyl or a hydrido cobalt carbonyl. By "cobalt carbonyl" we intend to define a compound containing only cobalt and carbon monoxide, such as $Co_2(CO)_8$ or $Co_4(CO)_{12}$. By "hydrido cobalt carbonyl" we intend to define a compound containing only cobalt, carbon monoxide and hydrogen, such as $HCo(CO)_4$. By "cobalt-containing material convertible to a cobalt carbonyl or a hydrido cobalt carbonyl" we intend to define any material which when mixed with hexane and subjected to 4000 pounds per square inch gauge (27.6 MPa) in an atmosphere containing hydrogen and carbon monoxide in a molar ratio of 1:1 at 150° to 200° C. for a period of three hours will result in the formation of a cobalt carbonyl, a hydrido cobalt carbonyl or mixtures thereof. Specific examples of a cobalt-containing material so convertible to a cobalt carbonyl or a hydrido cobalt carbonyl include cobalt(II) sulfate, cobalt oxide ($Co_3O_4$), cobalt(II)tetrafluoroborate, cobalt(II)acetate, cobalt(II)oxalate, cobalt(II)propionate, cobalt(II)octoate, cobalt(II)butyrate, cobalt(II)benzoate, cobalt(II)valerate, cobalt(II)formate, cobalt(II)cyclohexanebutyrate, cobalt(II)2-ethyl-hexaoate, cobalt(II)gluconate, cobalt(II)lactate, cobalt(II)naphthenate, cobalt(II)oleate, cobalt(II)citrate, cobalt(II)acetylacetonate, etc.

The relative amounts of carbon monoxide and hydrogen employed can be varied over a wide range. However, in general, the molar ratio of carbon monoxide to hydrogen is from about 2:1 to about 1:2, preferably about 1.5:1 to about 1:1.5, but most preferably about 1.25:1 to about 1:1.25. Compounds or reaction mixtures which give rise to the formation of carbon monoxide and hydrogen under the reaction conditions defined herein can be used instead of mixtures comprising carbon monoxide and hydrogen which are used in the preferred embodiments of this invention.

In order to obtain a product herein that predominates in aldehydes, particularly acetaldehyde, the amount of cobalt employed relative to the ligand and to iodine is critical. Thus, the molar ratio of cobalt, based on the element cobalt, to the ligand must be in the range of about 1:2 to about 7:1, preferably about 1:1.5 to about 4:1. The molar ratio of cobalt, based on the element cobalt, to iodine, based on the element iodine, must be in the range of about 1:1.15 to 1:15, preferably about 1:1.25 to about 1:5. Based on the methanol introduced into the system, the weight percent of combined cobalt and iodine, in their elemental form, can range from about 0.01 to about 10 percent, preferably from about 0.1 to about five percent.

The process herein can be carried out either in a batch operation or by passing the reactants continuously through a reaction zone. In each case the reactor is provided with agitation means and the pressure is maintained therein by the addition of hydrogen and carbon monoxide, or compounds producing hydrogen and carbon monoxide, as required. In order to facilitate the introduction of the phosphorus-containing ligand and the cobalt and iodine entities into the reaction zone and/or to facilitate recovery of the components of the reaction herein, they can be dissolved in an inert solvent, such as ethylene glycol, diethylene glycol monomethyl ether, acetone, sulfolanes, such as tetramethylene sulfone, lactones, such as γ-butyrolactone and ε-caprolactone, etc.

In the reaction zone the contents thereof are maintained at an elevated temperature and at an elevated critical pressure for a time sufficient to convert methanol to the desired aldehydes. The total pressure (based on hydrogen, carbon monoxide and any produced gases) must be at least about 2200 pounds per square inch gauge (15.02 MPa) but need not be in excess of about 10,000 pounds per square inch gauge (68.30 MPa). Especially desirable are pressures in the range of about 2500 pounds per square inch gauge (17.07 MPa) to about 7500 pounds per square inch gauge (51.19 MPa). Temperatures which are suitable for use herein are those temperatures which initiate a reaction between the reactants herein to selectively produce aldehydes, generally from about 150° to about 250° C., preferably from about 170° to about 220° C. The reaction is conducted for a time period sufficient to convert methanol to aldehydes, normally from about five minutes to about five hours, preferably from about ten minutes to about 2.5 hours.

Recovery of the desired aldehydes, for example acetaldehyde, from the reaction product can be effected in any convenient or conventional manner, for example, by distillation, at ambient pressure and about 21° C. The components will distill off in the following sequence for the desired recovery: acetaldehyde, propionaldehyde, methyl acetate, methanol, butyraldehyde, ethylacetate, ethanol, etc.

DESCRIPTION OF PREFERRED EMBODIMENTS

A series of 27 runs was carried out as follows. Into a 300 cc. stainless steel autoclave, equipped with agitation means, were charged 100 milliliters of methanol, 10 millimols of cobaltous acetylacetonate, and selected amounts of iodine and a phosphorus-containing ligand. In each of Runs Nos. I to XIX and XXIII to XXVII 10 millimols of iodine were used. In Runs Nos. XX, XXI and XXII, 6.25, 5.0 and 2.5 millimols of iodine, respectively, were used. In each of Runs Nos. I to X, XIII, XV to XVII and XX to XXVII 5 millimols of ligand were used. In each of Runs Nos. XI and XVIII 2.5 millimols of ligand were used. In Runs Nos. XII and XIV 3.7 millimols of ligand were used and in Run XIX 10 millimols of ligand were used. The reactor was next purged twice with nitrogen gas and then pressurized with carbon monoxide and hydrogen to a pressure of about half the desired reaction pressure. The system was then heated to a temperature of 200° C. and the pressure was adjusted to the reaction pressure, while maintaining selected molar ratios of carbon monoxide to hydrogen in the reaction zone, and such pressure was maintained throughout the reaction period. At the end of the reaction period the reactor contents were cooled by an internal cooling coil to about −75° C. The reactor was vented through a dry gas meter and a gas sample was taken for a mass spectral analysis and the liquid product was then analyzed by gas chromatography. The data obtained are set forth below in Tables II and III.

TABLE II

| Run No. | Phosphorus-Containing Ligand[a] | | | | | | Co:Ligand Molar Ratio | Co:I Molar Ratio | $CO:H_2$ | Pressure PSIG (MPa) | Reaction Time, Hours | Percent[b] MeOH Converted |
|---|---|---|---|---|---|---|---|---|---|---|---|---|
| | $R_1R_2$ | $R_3R_4$ | $R_5$ | E | x | n | | | | | | |
| I | Phenyl | Hydrogen | Phenyl | P | 1 | 1 | 2:1 | 1:2 | 1:1 | 4000(27.3) | 1.0 | 66 |
| II | Phenyl | Hydrogen | Phenyl | P | 1 | 2 | 2:1 | 1:2 | 1:1 | 4000(27.3) | 1.0 | 84 |
| III | Phenyl | Hydrogen | Phenyl | P | 1 | 2 | 2:1 | 1:2 | 1:2 | 4000(27.3) | 1.0 | 75 |
| IV | Phenyl | Hydrogen | Phenyl | P | 1 | 2 | 2:1 | 1:2 | 1:1 | 4000(27.3) | 1.5 | 91 |
| V | Phenyl | Hydrogen | Phenyl | P | 1 | 2 | 2:1 | 1:2 | 1:1 | 2000(13.65) | 2.5 | 59 |
| VI | Phenyl | Hydrogen | Phenyl | P | 1 | 3 | 2:1 | 1:2 | 1:1 | 4000(27.3) | 1.0 | 73.2 |
| VII | Phenyl | Hydrogen | Phenyl | P | 1 | 4 | 2:1 | 1:2 | 1:1 | 4000(27.3) | 1.0 | 67.8 |
| VIII | Phenyl | Hydrogen | Phenyl | P | 1 | 5 | 2:1 | 1:2 | 1:1 | 4000(27.3) | 1.5 | 68.0 |
| IX | Phenyl | Hydrogen | Phenyl | P | 1 | 6 | 2:1 | 1:2 | 1:1 | 4000(27.3) | 1.5 | 71.0 |
| X | Phenyl | Hydrogen | Phenyl | P | 2 | 2 | 2:1 | 1:2 | 1:1 | 4000(27.3) | 2.0 | 94.0 |
| XI | Phenyl | Hydrogen | Phenyl | P | 3 | 2 | 4:1 | 1:2 | 1:1 | 4000(27.3) | 1.0 | 87.0 |
| XII | Phenyl | Hydrogen | Phenyl | P | 3 | 2 | 2.7:1 | 1:2 | 1:1 | 4000(27.3) | 1.0 | 92.0 |
| XIII | Phenyl | Hydrogen | Phenyl | P | 3 | 2 | 2:1 | 1:2 | 1:1 | 4000(27.3) | 1.0 | 96.0 |
| XIV | Phenyl | Hydrogen | Phenyl | P | 3 | 2 | 2.7:1 | 1:2 | 1:1.5 | 4000(27.3) | 1.0 | 82.6 |
| XV | P—Tolyl | Hydrogen | P—Tolyl | P | 1 | 2 | 2:1 | 1:2 | 1:1 | 4000(27.3) | 1.0 | 70.0 |
| XVI | Ethyl | Hydrogen | Ethyl | P | 1 | 2 | 2:1 | 1:2 | 1:1 | 4000(27.3) | 1.0 | 91.6 |
| XVII | Phenyl | Hydrogen | Phenyl | P | 1 | 2 | 2:1 | 1:2 | 1:1 | 3000(20.48) | 2.0 | 83.0 |
| XVIII | Phenyl | Hydrogen | Phenyl | P | 1 | 2 | 4:1 | 1:2 | 1:1 | 4000(27.3) | 1.0 | 79.0 |
| XIX | Phenyl | Hydrogen | Phenyl | P | 1 | 2 | 1:1 | 1:2 | 1:1 | 4000(27.3) | 1.0 | 86.0 |
| XX | Phenyl | Hydrogen | Phenyl | P | 1 | 2 | 2:1 | 1:1.25 | 1:1 | 4000(27.3) | 1.0 | 80.0 |
| XXI | Phenyl | Hydrogen | Phenyl | P | 1 | 2 | 2:1 | 1:1 | 1:1 | 4000(27.3) | 1.0 | 78.0 |
| XXII | Phenyl | Hydrogen | Phenyl | P | 1 | 2 | 2:1 | 2:1 | 1:1 | 4000(27.3) | 1.0 | 66.0 |
| XXIII | Phenyl | $R_3 \neq R'_3; R_4 = R'_4$ $R_3 =$ Methyl $R'_3 =$ Hydrogen $=$ $R_4 = R'_4$ | Phenyl | P | 1 | 2 | 2:1 | 1:1 | 1:1 | 4000(27.3) | 1.0 | 94.8 |
| XXIV | Phenyl | $R_3 = R'_3 =$ Methyl $R_4 = R'_4 =$ Hydrogen | Phenyl | P | 1 | 2 | 2:1 | 1:2 | 1:1 | 4000(27.3) | 1.0 | 89.2 |
| XXV | Phenyl | Hydrogen | Phenyl | As | 1 | 2 | 2:1 | 1:2 | 1:1 | 4000(27.3) | 1.0 | 27.0 |
| XXVI | Phenyl | Hydrogen | Phenyl | As | 1 | 2 | 2:1 | 1:2 | 1:2 | 4000(27.3) | 1.0 | 61.0 |
| XXVII | $R_1 = R'_1 =$ $R_2 =$ Phenyl $R'_2 =$ $(C_6H_5)_2PCH_2CH_2-$ | Hydrogen | Phenyl | P | 2 | n | 2:1 | 1:2 | 1:2 | 4000(27.3) | 1.0 | 86.5 |

(a)

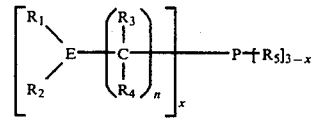

(b)Methanol, $CH_3OH$

TABLE III

| Run No. | $Me_2O$[c] | HAc[d] | MeF[e] | EtOH[f] | $Et(OMe)_2$[g] | EtCHO[h] | MeOAc[i] | PrCHO[j] |
|---|---|---|---|---|---|---|---|---|
| I | 7.4 | 30.4 | 0.1 | 0.5 | 1.1 | 1.2 | 28.7 | 7.8 |
| II | 4.6 | 49.7 | 1.5 | 1.1 | 1.2 | 0.6 | 18.4 | 13.1 |
| III | 9.2 | 43.1 | 2.1 | 14.0 | 4.5 | 3.1 | 8.4 | 11.8 |
| IV | 3.7 | 40.0 | 0.6 | 5.1 | 1.5 | 0.3 | 18.6 | 21.2 |

TABLE III-continued

| Run No. | | | | | | | | |
|---|---|---|---|---|---|---|---|---|
| V | 49.7 | 9.1 | 0.6 | 1.0 | 1.4 | 1.6 | 21.1 | 4.3 |
| VI | 7.3 | 30.6 | 0.2 | 0.8 | 0 | 4.0 | 25.7 | 7.6 |
| VII | 10.5 | 23.6 | 0.8 | 2.0 | 9.1 | 1.8 | 24.2 | 6.4 |
| VIII | 31.0 | 23.7 | 0.7 | 2.2 | 1.1 | 0.2 | 10.3 | 12.4 |
| IX | 30.1 | 16.0 | 0.4 | 0.8 | 1.9 | 1.7 | 16.4 | 5.8 |
| X | 4.2 | 35.9 | 0.2 | 2.8 | 0 | 1.1 | 13.9 | 17.4 |
| XI | 8.6 | 45.0 | 0 | 0.9 | 0 | 1.8 | 21.0 | 13.9 |
| XII | 9.8 | 51.3 | 0 | 0.9 | 0 | 0.8 | 17.4 | 13.1 |
| XIII | 7.8 | 53.7 | 0 | 0.4 | 0 | 1.9 | 14.0 | 10.5 |
| XIV | 12.7 | 53.7 | 0 | 0.8 | 0 | 0.6 | 11.5 | 10.7 |
| XV | 9.0 | 29.4 | 0.3 | 1.2 | 1.5 | 1.0 | 25.6 | 7.3 |
| XVI | 5.4 | 45.3 | 0.04 | 0 | 0.4 | 1.7 | 20.0 | 15.1 |
| XVII | 11.1 | 36.4 | 0.6 | 1.2 | 3.0 | 0.5 | 20.8 | 17.4 |
| XVIII | 2.1 | 31.7 | 1.1 | 8.8 | 5.2 | 0.6 | 27.6 | 11.5 |
| XIX | 1.5 | 43.9 | 1.1 | 17.6 | 0.3 | 1.4 | 18.2 | 8.3 |
| XX | 2.6 | 33.6 | 0.6 | 13.7 | 1.1 | 1.6 | 24.6 | 6.3 |
| XXI | 2.2 | 20.4 | 0.9 | 28.9 | 2.2 | 0.5 | 21.1 | 8.6 |
| XXII | 2.3 | 22.2 | 1.2 | 36.9 | 4.5 | 2.1 | 22.1 | 1.5 |
| XXIII | 1.0 | 42.8 | 0.2 | 1.4 | 0.9 | 1.6 | 21.5 | 18.3 |
| XXIV | 2.4 | 43.5 | 0.2 | 3.5 | 0.8 | 0.8 | 23.1 | 18.3 |
| XXV | 4.9 | 37.0 | 0.1 | 1.0 | 1.9 | 5.6 | 28.8 | 7.8 |
| XXVI | 28.1 | 27.8 | 4.1 | 2.0 | 2.0 | 6.4 | 11.8 | 5.8 |
| XXVII | 7.8 | 50.7 | 0 | 0 | 0.5 | 1.2 | 23.6 | 10.7 |

| Run No. | EtOAc[k] | HOAc[l] | Others[m] | Total Weight Percent Aldehydes[n] | Total Weight Percent Alcohols[o] |
|---|---|---|---|---|---|
| I | 1.8 | 0 | 21.0 | 57.3 | 6.5 |
| II | 0 | 2.4 | 7.3 | 71.4 | 2.6 |
| III | 1.1 | 0 | 2.6 | 64.6 | 15.7 |
| IV | 4.3 | 0.4 | 4.2 | 66.6 | 10.1 |
| V | 0 | 0 | 10.8 | 23.8 | 3.2 |
| VI | 0.8 | 0 | 22.9 | 60.5 | 6.2 |
| VII | 1.3 | 0 | 20.1 | 57.0 | 7.4 |
| VIII | 0 | 0 | 18.3 | 53.5 | 6.1 |
| IX | 0 | 0 | 26.9 | 47.0 | 6.1 |
| X | 4.8 | 0 | 19.7 | 72.8 | 8.9 |
| XI | 1.5 | 0 | 7.3 | 66.6 | 2.3 |
| XII | 1.7 | 0 | 4.9 | 69.2 | 3.6 |
| XIII | 3.1 | 0 | 8.5 | 72.1 | 4.6 |
| XIV | 1.3 | 0 | 8.6 | 70.3 | 3.4 |
| XV | 3.0 | 0 | 21.7 | 56.5 | 8.6 |
| XVI | 6.3 | 0 | 5.6 | 67.0 | 7.5 |
| XVII | 2.6 | 0 | 6.5 | 59.5 | 8.1 |
| XVIII | 6.4 | 1.1 | 3.9 | 52.2 | 15.9 |
| XIX | 7.0 | 0.3 | 0.2 | 54.3 | 24.8 |
| XX | 9.1 | 3.0 | 3.7 | 45.5 | 19.2 |
| XXI | 10.1 | 2.0 | 3.0 | 34.2 | 39.7 |
| XXII | 5.1 | 1.0 | 0.9 | 31.1 | 42.2 |
| XXIII | 7.6 | 0 | 4.0 | 67.2 | 9.3 |
| XXIV | 6.3 | 0 | 0 | 66.1 | 8.1 |
| XXV | 0 | 0 | 12.3 | 62.2 | 4.0 |
| XXVI | 0 | 0 | 11.8 | 51.3 | 6.2 |
| XXVII | 0 | 0 | 5.5 | 67.5 | 1.1 |

[c] Dimethyl ether $CH_3OCH_3$
[d] Acetaldehyde $CH_3CHO$
[e] Methyl formate $HCOOCH_3$
[f] Ethanol $C_2H_5OH$
[g] Dimethyl acetal $CH_3CH(OCH_3)_2$
[h] Propanol $C_2H_5CHO$
[i] Methyl acetate $CH_3COOCH_3$
[j] Butanal $C_3H_7CHO$
[k] Ethyl acetate $CH_3COOC_2H_5$
[l] Acetic acid $CH_3COOH$
[m] Mixtures of 1,1-dimethoxy ethane, 1,1-dimethoxy butane, 1,1-diethoxy ethane, diethylether, crotonaldehyde and other aldehyde condensation products
[n] Aldehydes + materials convertible to aldehydes, for example, by hydrolysis
[o] Alcohols + materials convertible to alcohols, for example, by hydrolysis That the operation herein must be carried out under the critical criteria of selected phosphorus-containing compounds, critical ratios of cobalt to iodide and critical operating pressures is apparent from each of Runs Nos. V, VII to IX, XXI and XXII, wherein each was carried outside the critical parameters defined herein and reaction products were obtained that failed to contain the desired amounts of aldehydes, including the desired amounts of acetaldehyde.

Obviously, many modifications and variations of the invention, as hereinabove set forth, can be made without departing from the spirit and scope thereof, and therefore only such limitations should be imposed as are indicated in the appended claims.

We claim:

1. A process for selectively producing aldehydes which comprises introducing into a reaction zone (1) methanol, (2) carbon monoxide, (3) hydrogen, (4) cobalt, (5) iodine, and (6) a phosphorus-containing ligand defined by the following formula:

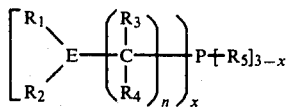

wherein $R_1$, $R_2$ and $R_5$ are either alike or different members selected from the group consisting of alkyl radicals having from one to 24 carbon atoms, aryl radicals having from six to 20 carbon atoms, alkenyl radicals having from two to 30 carbon atoms, cycloalkyl radicals having from three to 40 carbon atoms, cycloalkyl radicals having from three to 40 carbon atoms, aralkyl and alkaryl radicals having from six to 40 carbon atoms and dihydrocarbyl phosphino alkyl radicals, $R_3$ and $R_4$ are either alike or different members selected from the group consisting of hydrogen, alkyl radicals having from one to 24 carbon atoms, aryl radicals having from six to 20 carbon atoms, alkenyl radicals having from two to 30 carbon atoms, cycloalkyl radicals having from three to 40 carbon atoms, aralkyl and alkaryl radicals having from six to 40 carbon atoms, and dihydrocarbyl phosphino alkyl radicals, E is phosphorus, n is an integer ranging from 1 to 3, and x can be 1 to 3, the molar ratio of carbon monoxide to hydrogen being in the range of about 2:1 to about 1:2, the molar ratio of cobalt to said ligand being in the range of about 1:2 to about 7:1, the molar ratio of cobalt to iodine being in the range of about 1:1.15 to about 1:15, and the weight percent of combined cobalt and iodine, based on the methanol, being in the range of about 0.01 to about ten percent, and then subjecting said contents to an elevated temperature of about 150° to about 250° C. and an elevated pressure of at least about 2200 pounds per square inch for about five minutes to about five hours, sufficient to convert methanol to a product predominating in aldehydes.

2. The process of claim 1 wherein R1, R2 and R5 are either alike or different members selected from the group consisting of alkyl radicals having from two to ten carbon atoms, aryl radicals having from six to ten carbon atoms, alkenyl radicals having from two to 20 carbon atoms, cycloalkyl radicals having from three to 30 carbon atoms, aralkyl and alkaryl radicals having from six to 30 carbon atoms, and dihydrocarbyl phosphino alkyl radicals, R3 and R4 are either alike or different members selected from the group consisting of hydrogen, alkyl radicals having from two to ten carbon atoms, aryl radicals having from six to ten carbon atoms, alkenyl radicals having from two to 20 carbon atoms, cycloalkyl radicals having from three to 30 carbon atoms, aralkyl and alkaryl radicals having from six to 30 carbon atoms, and dihydrocarbyl phosphino alkyl radicals, E is phosphorus, n is an integer ranging from 2 to 3, x is 1, the molar ratio of carbon monoxide to hydrogen being in the range of about 1.5:1 to about 1:1.5, the molar ratio of cobalt to said ligand being in the range of about 1:1.5 to about 4:1, the molar ratio of cobalt to iodine being in the range of about 1:1.25 to about 1:5, and the weight percent of combined cobalt and iodine, based on the methanol, being in the range of about 0.1 to about five percent, and then subjecting said contents to an elevated temperature of about 170° C. to about 220° C. and an elevated pressure of from about 2500 to about 7500 pounds per square inch gauge for about ten minutes to about 2.5 hours, sufficient to convert methanol to a product predominating in aldehydes.

3. The process of claim 1 wherein n is 2 and the molar ratio of carbon monoxide to hydrogen is in the range of about 1.25:1 to about 1:1.25.

4. The process of claim 1 wherein $R_1$, $R_2$ and $R_5$ can be aryl or alkyl radicals.

5. The process of claim 1 wherein $R_1$, $R_2$ and $R_5$ are aryl radicals.

6. The process of claim 1 wherein $R_1$, $R_2$ and $R_5$ are alkyl radicals.

7. The process of claim 2 wherein $R_1$, $R_2$ and $R_5$ can be aryl or alkyl radicals.

8. The process of claim 2 wherein $R_1$, $R_2$ and $R_5$ are aryl radicals.

9. The process of claim 2 wherein $R_1$, $R_2$ and $R_5$ are alkyl radicals.

10. The process of claim 1 wherein $R_3$ and $R_4$ can be hydrogen or aryl or alkyl radicals.

11. The process of claim 1 wherein $R_3$ and $R_4$ are hydrogen.

12. The process of claim 1 wherein $R_3$ and $R_4$ are aryl radicals.

13. The process of claim 1 wherein $R_3$ and $R_4$ are alkyl radicals.

14. The process of claim 2 wherein $R_3$ and $R_4$ can be hydrogen or aryl or alkyl radicals.

15. The process of claim 2 wherein $R_3$ and $R_4$ are hydrogen.

16. The process of claim 2 wherein $R_3$ and $R_4$ are aryl radicals.

17. The process of claim 2 wherein $R_3$ and $R_4$ are alkyl radicals.

18. The process of claim 1 wherein R1, R2 and R5 are phenyl radicals, $R_3$ and $R_4$ are hydrogen, x is 1, n is 1, the molar ratio of cobalt to ligand is about 2:1 and the molar ratio of cobalt to iodide is about 1:2.

19. The process of claim 18 wherein n is 2.

20. The process of claim 18 wherein n is 3.

21. The process of claim 18 wherein x is 2 and n is 2.

22. The process of claim 18 wherein x is 3 and n is 2.

23. The process of claim 19 wherein $R_1$, $R_2$ and $R_5$ are p-tolyl.

24. The process of claim 19 wherein $R_1$, $R_2$ and $R_5$ are ethyl.

* * * * *